United States Patent
Zhang

(10) Patent No.: US 10,064,710 B2
(45) Date of Patent: Sep. 4, 2018

(54) ORAL HYGIENE APPARATUS

(71) Applicant: Winston Zhang, Irvine, CA (US)

(72) Inventor: Winston Zhang, Irvine, CA (US)

(*) Notice: Subject to any disclaimer, the term of this patent is extended or adjusted under 35 U.S.C. 154(b) by 0 days.

(21) Appl. No.: 15/046,336

(22) Filed: Feb. 17, 2016

(65) Prior Publication Data

US 2016/0157974 A1   Jun. 9, 2016

Related U.S. Application Data

(63) Continuation-in-part of application No. 13/945,036, filed on Jul. 18, 2013.

(51) Int. Cl.
*A61C 17/00*  (2006.01)
*A61C 17/02*  (2006.01)

(52) U.S. Cl.
CPC .......... *A61C 17/0214* (2013.01); *A61C 17/02* (2013.01); *A61C 17/0202* (2013.01)

(58) Field of Classification Search
CPC .. A61C 17/0214; A61C 17/0202; A61C 17/02
See application file for complete search history.

(56) References Cited

U.S. PATENT DOCUMENTS

| | | | | |
|---|---|---|---|---|
| 3,593,962 A * | 7/1971 | Sullivan | ............ | A61C 17/0214 251/343 |
| 4,043,337 A * | 8/1977 | Baugher | ............ | A61C 17/0214 601/162 |
| 5,220,914 A * | 6/1993 | Thompson | ......... | A61C 17/0214 601/155 |
| 5,484,281 A * | 1/1996 | Renow | ............... | A61C 17/0214 433/80 |
| 7,276,035 B2 * | 10/2007 | Lu | ..................... | A61C 17/0202 433/80 |
| 7,344,510 B1 * | 3/2008 | Yande | ................ | A61C 17/0214 433/80 |
| 8,047,840 B2 * | 11/2011 | Shaw | ................. | A61C 17/0202 433/80 |
| 2008/0078021 A1 * | 4/2008 | Welch | ................... | E03C 1/0401 4/675 |
| 2009/0163839 A1 * | 6/2009 | Alexander | ......... | A61C 17/0214 601/165 |
| 2013/0149662 A1 * | 6/2013 | Meloul-Tzubeli | ..... | A61C 17/00 433/80 |

* cited by examiner

*Primary Examiner* — Steven Douglas

(57) ABSTRACT

An oral hygiene apparatus in the form of a fixture to provide a controllable pressurized water stream for cleansing the gums and teeth, especially in the interdental area, of a user. The hygiene apparatus may essentially comprise three parts including a water supply, an oral hygiene-ware and a water utility.

1 Claim, 5 Drawing Sheets

ORAL HYGIENE APPARATUS

CROSS-REFERENCE TO RELATED APPLICATIONS

U.S. patent application Ser. No. 13/945,036 dated on Jul. 18, 2013 the contents of which are hereby incorporated by reference.

FIELD OF INVENTION

The field of the invention is oral hygiene devices.

BACKGROUND OF THE INVENTION

A significant public health problem: one out of every two American adults aged 30 and over has periodontal disease, according to August 2012 released findings from the Centers for Disease Control and Prevention (CDC). Some of developing countries have more than 90% of adults have periodontal disease. Periodontal disease is a chronic inflammatory disease that affects the gum tissue, bone supporting the teeth and tooth loss. Periodontal disease is associated with other chronic inflammatory diseases, such as diabetes and cardiovascular disease. Although brushing and flossing are the primary tools for oral clean, but brush and floss remove up to 70% plaque according to Sunstar Suisse S.A.

Oral irrigators especially a water jet system could remove most of plaque. USC study finds dental water jet removes 99.9 percent of dental plaque biofilm. This was released at February 2009 from University of Southern California School of Dentistry.

Various water irrigating oral hygiene devices have been in the market or have had patent proposals. For example, Water Pik from Water Pik, Inc. needs to use electricity or battery for power. Alexander, U.S. Pat. No. 8,012,111, proposed a sink fixture have a flexible tubing 175 for hot and cold water and temperature control 120. They are extras to the adjacent faucet, not only more costly to manufacture and maintain but also makes housing 110 heavy to hold.

The present invention satisfies the shortcomings, limitations or disadvantages of all water irrigating oral hygiene devices in the market and patent proposals in the prior art.

CROSS REFERENCE

| U.S. Patent Documents | | |
|---|---|---|
| 6056710 | May 2000 | Bachman |
| 6740053 | May 2004 | Kaplowitz |
| 6783364 | August 2004 | Juan |
| 6835181 | December 2004 | Hippensteel |
| 2007/0203439 | August 2007 | Boyd et al. |
| 2007/0261163 | November 2007 | Lynam |
| 2004/0045107 | March 2004 | Egeresi |
| 2006/0010624 | January 2006 | Cleland |
| 2006/0048791 | March 2006 | Mehes et al. |
| 2008/0078021 | April 2008 | Welch |
| 2009/0053672 | February 2009 | Cornelius |
| 8012111 | September 2011 | Alexander |
| 8114038 | February 2012 | Stelmach |
| 8449295 | May 2013 | Hegemann |

SUMMARY OF THE INVENTION

The present invention, oral hygiene apparatus, forms a fixture to provide a controllable pressurized water stream for cleansing gums and teeth especially the interdental area. Meanwhile, it provides water utility similar to faucets or showers. The oral hygiene apparatus may comprise three parts: a water supply, an oral hygiene-ware and a water utility.

The water supply part may have a pair of hoses and a mixer valve and an outlet. The hoses connect to the cold and hot water supply from the wall and couple to a mixer valve. The mixer valve will mix the cold and hot water, controls water temperature and controls water flow rate. The mixed water will flow out of an outlet. The outlet will connect to an oral hygiene-ware and the water utility.

The oral hygiene-ware may have a soft hose, a handle and tips. The soft hose in the oral hygiene-ware should be flexible with proper dimensional size and be long enough for oral hygiene purposes. The soft hose connects to a connection point from the water supply to receive water. The handle is coupled with the soft hose. The handle has a built-in valve and a quick connector. The valve in the handle will control flow rate and be able to shut off the water flow. The quick connector has a mechanism that allows a user to change between different tips. Each of the tips has special oral hygiene function. For example, the waterjet brush tip has nozzles and bristle tufts in the head. The waterjet ejected from the nozzles and brushing will significantly improve cleaning of the teeth especially in the interdental area. A swirl waterjet tip could generate a waterjet beam and a swirl waterjet. The swirl waterjet can do deep dental cleansing even inside a periodontal pocket.

The mixed water from water supply into the oral hygiene-ware is then ejected out through a tip into the mouth of user for oral hygiene.

The water utility has a hose, a pipe, a valve and a utility head. The hose connects the outlet of the water supply and is coupled to the pipe. The pipe will deliver the water to the utility head. The valve can be installed in any portion of the water utility and could shut off the water flow. A connector in the end of the pipe could connect to a utility head. The utility head could be a filter, nozzles, showerhead etc.

The mixed water from the water supply will flow into the water utility then flow out from the utility head for utility purpose.

For hygiene-ware to properly function the water utility could be turned on or off. The water utility shut off can be done manually or automatically.

The oral hygiene apparatus according the present invention generates waterjet without electricity, batteries or other power sources. It is "green" and environmentally friendly.

The oral hygiene apparatus in one embodiment is preferably a fixture in the bathroom. The water utility of the oral hygiene apparatus could be a portion of a faucet or shower. The oral hygiene apparatus does not need a counter top, does not need a reservoir, and does not create noise.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

FIG. 2 is a schematic showing an embodiment of the oral hygiene apparatus.

FIG. 3-1 is a schematic showing the hygiene-ware.

FIG. 3-2 is a schematic showing the hygiene-ware tips.

FIG. 3-3 is a schematic showing the swirl waterjet tip.

FIG. 3-4 is a schematic showing the waterjet brush tip.

FIG. 4 is a schematic showing the structure of a valve in the utility

DESCRIPTION OF THE PREFERRED EMBODIMENTS

Figure 1:
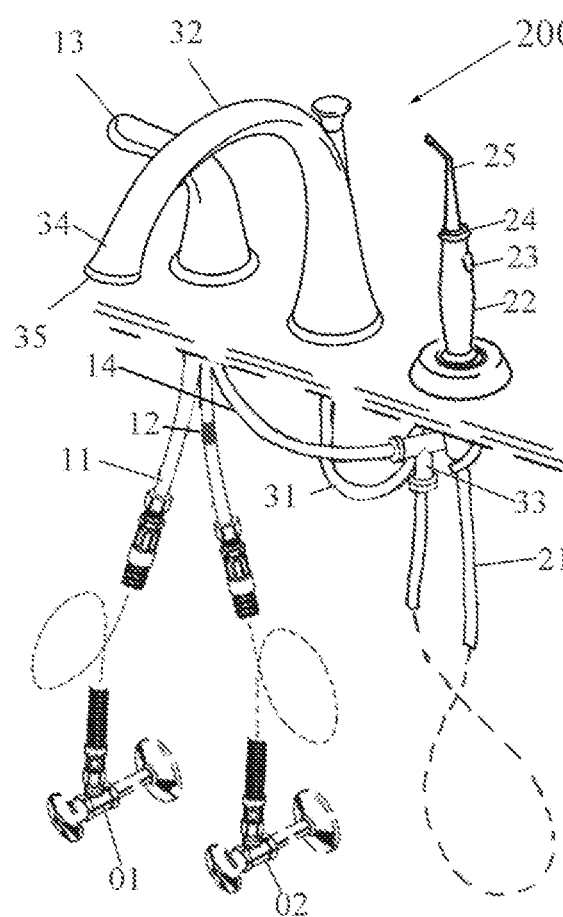
FIGS. 1-1 and 1-2 are schematics showing the oral hygiene apparatus.
Figures 1, 2:
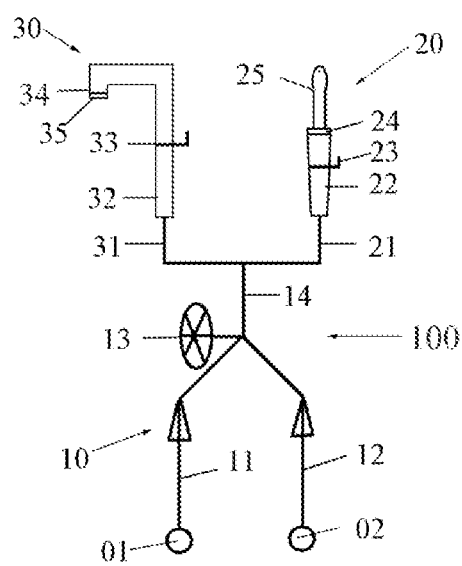
Figure 2:
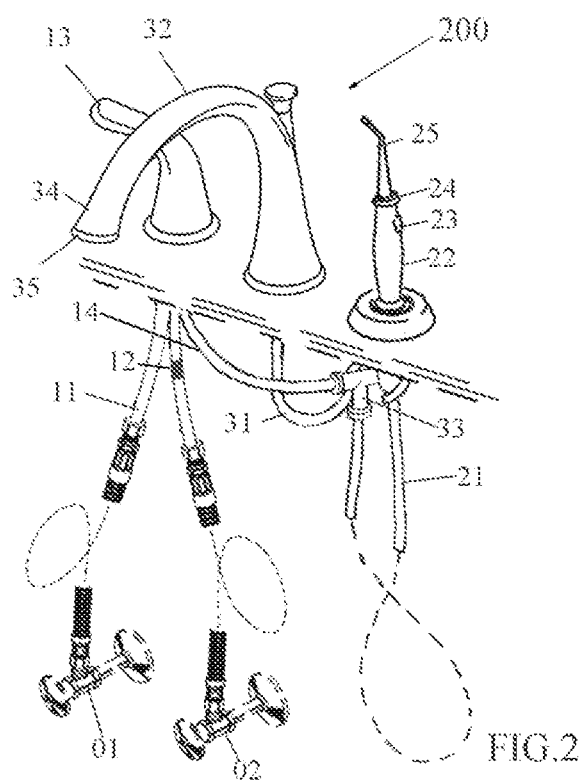

With reference to FIGS. 1-1 and 1-2, an oral hygiene apparatus 100 generally comprises a water supply part 10, an oral hygiene-ware part 20 and water utility part 30.

The water supply part 10 may have a pair of hoses 11 and 12, a mixer valve 13 and an outlet 14. The hoses 11 and 12 connect to cold and hot water suppliers 01 and 02, respectively, from a water supply and coupled to the mixer valve 13. The mixer valve 13 will mix the cold and hot water, controls water temperature and control water flow rate. The mixed water will flow out at an outlet 14. The outlet 14 will connect to the oral hygiene-ware part 20 and the water utility 30. For example, a shower water supply that is built into a wall can be used as the water supply part 10.

The oral hygiene-ware part 20 may have a soft hose 21, a handle 22 and exchangeable tips 25. The soft hose 21 should be flexible with proper diameter and long enough for oral hygiene purpose. The soft hose 21 diameter is preferably between 2 mm to 1.5 cm. The soft hose 21 length is preferably between 50 cm to 2 m. The soft hose 21 connects to the outlet 14 of the water supply part 10 to receive the mixed water. The handle 22 is coupled to the soft hose 21. The handle 22 has a built-in valve 23 and a quick connector 24. The built-in valve 23 in the handle controls mixed water flow rate and can shut off the water flow. The quick connector 24 has a mechanism that can quickly exchange the exchangeable tips 25. The mixed water will flow through the handle 22 and pass through the quick connector 24 and then through the exchangeable tips 25 out to the mouth of user. Each exchangeable tip 25 has special oral hygiene functions. For example, the swirl waterjet tip 251 could generate a waterjet beam and a swirl waterjet, FIG. 3-3. The swirl waterjet can do deep dental cleansing even inside the periodontal pocket. The waterjet brush tip 255 has nozzles 552 and bristle tufts 551 in the head of the tip, refers to FIG. 3-4. The waterjet ejected from the nozzles 552 and brushing by the bristle tufts 551 will significantly increase cleansing the plaque on the teeth especially in the interdental area. Nozzles 552 should have a height of 0.2-4 millimeters less than the bristle tufts 551 that can vary in length from 5-15 millimeters preferably 10 millimeters. Further, the opening at the end of the nozzle 552 is 0.3-0.8 millimeters in diameter. The waterjets described herein are intended to have a force of 60-200 PSI. The nozzle 552 is shorter than the bristle tufts to maximize the accuracy of the waterjets and help guide a user to avoid placing the waterjet onto the or below the gumline.

The mixed water from water supply part 10 flows into the oral hygiene-ware 20 and then ejects out from the exchangeable tip 25 into the month of user to perform oral hygiene functioning.

The water utility part 30 may have a hose 31, a pipe 32, a valve 33 and connector 34 which connects to a utility head 35. The hose 31 connects to the outlet 14 of the water supply part 10 and pipe 32. The pipe 32 will deliver the water to the utility head 35. There is valve 33 installed in the pipe 32 and controls water flow rate. The valve 33 could be installed in any portion of the water utility part 30. The connector 34 in the end of the pipe 32 could connect the utility head 35. The utility head 35 could be a filter, nozzles, showerhead etc.

The mixed water from the water supply part 10 flows into the water utility 20 then flows out for water utility purpose.

With reference to FIG. 2, it shows an embodiment of oral hygiene apparatus 200. The oral hygiene apparatus 200 could be installed in a bathroom as a sink fixture. The oral hygiene apparatus 200 may have a water supply that comprises hoses 11 and 12. The hoses 11 and 12 could connect water supplies 01 and 02 from a wall mounted valve to receive cold and hot water. The hoses 11 and 12 coupled with mixer valve 13. The water mixer valve 13 adjusts water temperature to a proper temperature for the user. The water flow rate could also be controlled by the mixer valve 13. The mixed water will flow out at the outlet 14 to oral hygiene-ware 20 and water utility 30.

The oral hygiene apparatus 200 may have an oral hygiene-ware that comprises hose 21. The mixed water from the outlet 14 will flow into the hose 21. The hose 21 is coupled to the handle 22. There is a built-in valve 23 that is inside the handle 22. The built-in valve 23 could control the mixed water flow out pressure by adjusting the flow rate. At a proximate end of the handle 22 may have a quick connector 24 which could quickly exchange exchangeable tips 25. The mixed water will flow from handle 22 to the exchangeable tip 25 out to the user's mouth. Various tips may be available for oral hygiene functioning.

Figures 1, 3:
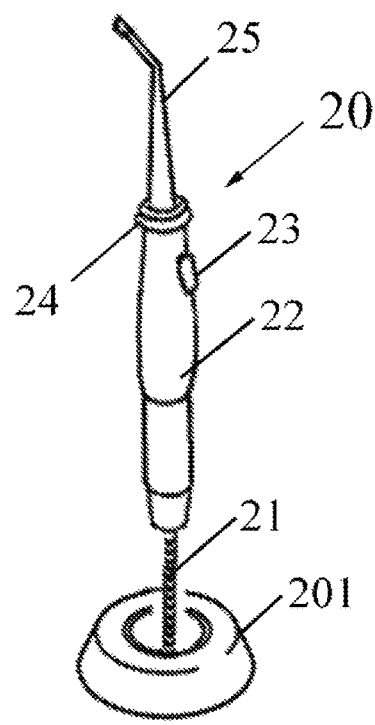
Figures 2, 3:
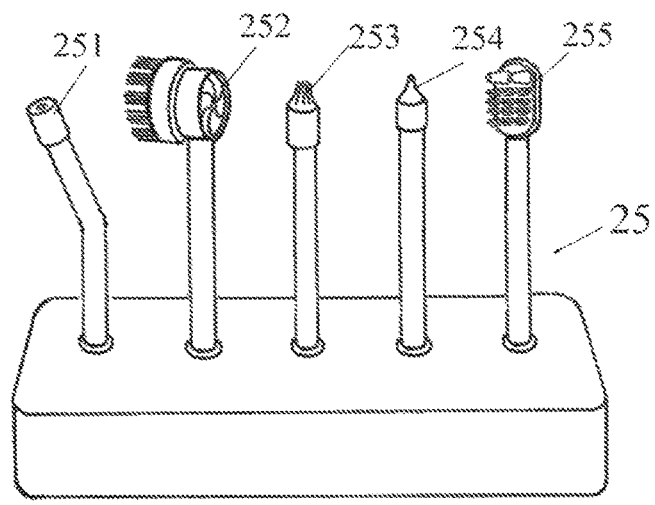
Figure 3:
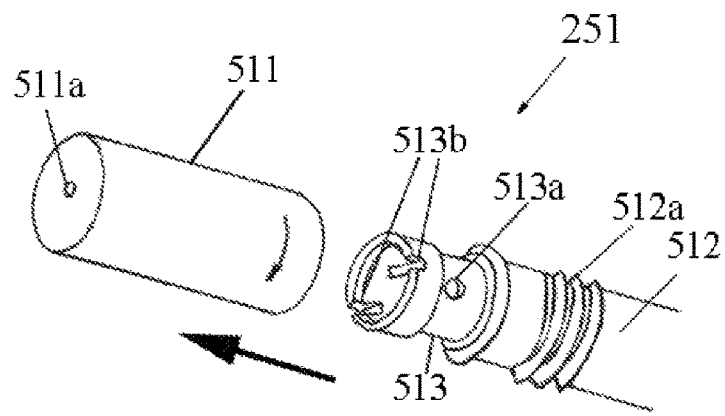
Figures 3, 4:
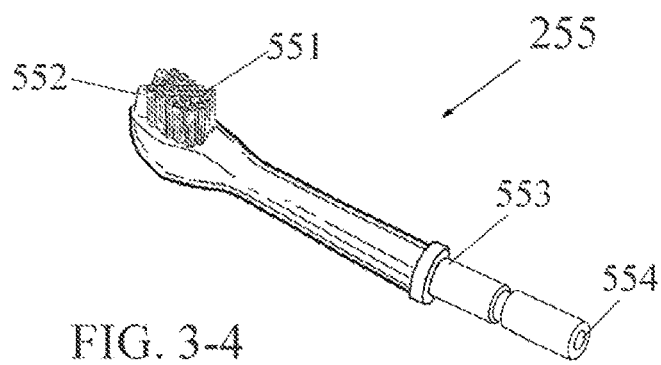
Figure 4:
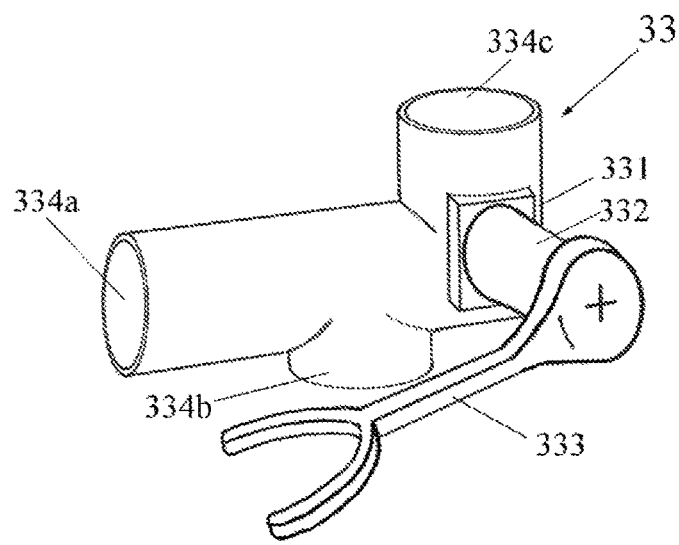

FIG. 3-2 depicts some exchangeable tips 25 but is not intended to be limiting. Such as swirl waterjet tip 251, refers to FIG. 3-3; rotatable brush tip 252; gumline brush tip 253; an interdental brush tip 254 and waterjet brush tip 255, refers FIG. 3-4.

The oral hygiene apparatus 200 may have a water utility that comprises a hose 31, a valve 33, pipe 32, connector 34 and utility head 35. The mixed water from the outlet 14 will flow into the valve 33 in the water utility. The valve 33 connects to the hose 31 that is coupled to the pipe 32. The valve 33 may shut off automatically by raising the handle 22. The pipe 32 will deliver the water to utility head 35. At the proximal end of the pipe 32 may have a connector 34 for mounting the utility head 35.

To use the oral hygiene apparatus 200 for oral hygiene the user should first select an exchangeable tip. The tip 255 is recommended for general cleaning. If the user has periodontal disease the tip 251 should be used after the tip 255. After a user selects a tip and installed in the handle 22, user should turn on the mixer valve 13 and check the water temperature from out of the utility head 35. When the temperature is preferred, raising the handle 22 and the arm 333 will lift, FIG. 4. The lifted arm 333 will shut off the valve 33 and no more water will flow out from the outlet 334c. When the lifted arm 333 is lifted, water flow to the utility head 35 is stopped, FIG. 4. Then the user can use the hygiene-ware freely.

The tip 255 has nozzles 552 and bristle tufts 551 in the head of the tip 255. The nozzles 552 will eject a waterjet. The tip 255 has a connector 553 and water inlet 554 refers to FIG. 3-4. The nozzles 552 are narrowed top conical tube made of elastomer or flexible material. The nozzles 552 can detect the position on the teeth to directing waterjet & brushing and avoid bristle tufts 551 from passing beyond the gumline to harm the gum.

For a user who has periodontal disease the tip 251 is recommended. The tip 251 comprises tube 512 and cap 511 with one hole 511a in the cap 511 refers to FIG. 3-3. There is a swirl waterjet generator 513 in the front of the tube 512.

There are two holes 513a to allow water out from tube 512 then through two parallel tangent lines 513b out to cap 511. For the sake of clarity the two holes 513a are parallel but do not pass through a diameter of the swirl waterjet generator 513. Water exiting from tangent lines 513b twist relative to one another causing a swirl waterjet. When the cap 511 is screwed tightly onto the tube 512, a swirl waterjet will eject out from the hole 511a. When the cap 511 is screwed onto the tube 512 in a slightly loose position, the waterjet beam will eject out from the hole 511a. Water will flow into tube 512 from handle 22 then through the swirl waterjet generator 513 to eject waterjet beam or swirl waterjet to mouth of user to cleansing gingival area and dental pockets.

Figure 5:
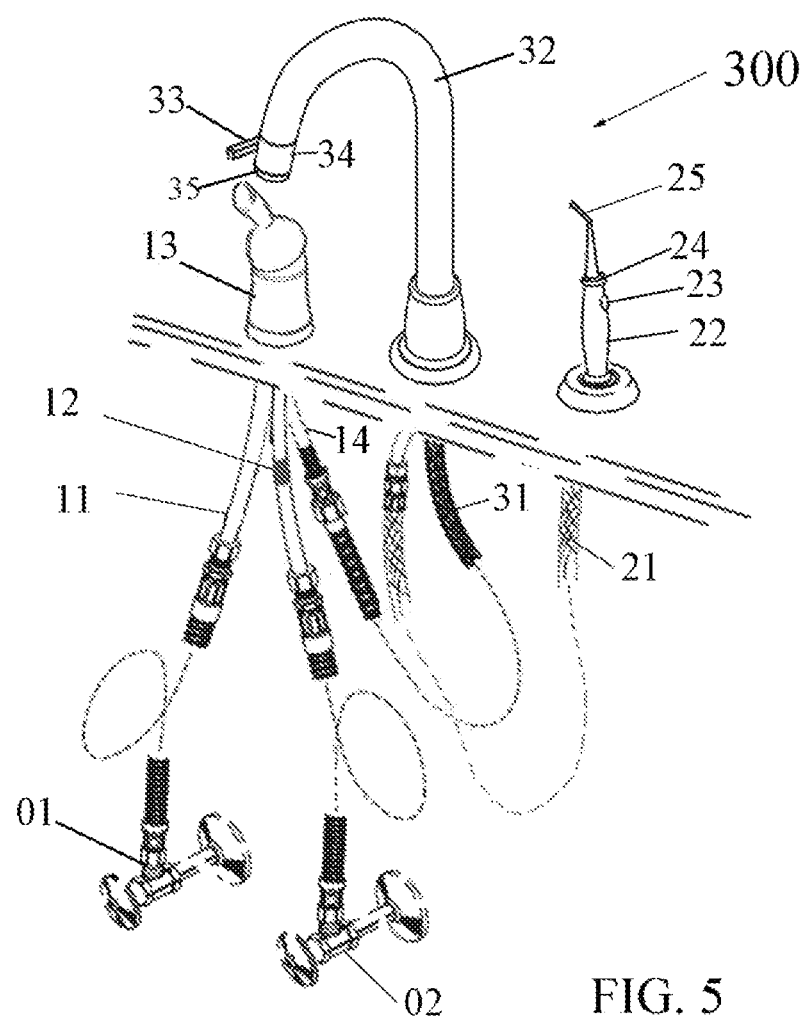
FIG. 5 is a schematic showing another preferred embodiment of the oral hygiene apparatus wherein there is a manual shut-off function.

With reference to FIG. 5, it shows another preferred embodiment of oral hygiene apparatus 300. This preferred embodiment one places the valve 33 in the water utility and utility head 35. The valve 33 is a manually operated and installed at the outlet of the pipe 32. The hose 21 and hose 31 will be installed accordingly. The utility head 35 is a spray nozzle. The spray nozzle 35 could save water up to 70% than regular faucet.

In preferred embodiments, the oral hygiene-ware devices will not need electricity or other energy source. It is greenness and environment friendly.

Thus, specific embodiments and applications of oral hygiene apparatus have been disclosed. It should be apparent, however, to those skilled in the art that many more modifications beside those already described are possible without departing from the inventive concepts herein. The inventive subject matter, therefore, is not to be restricted except in the spirit of the appended claims. Moreover, in interpreting both the specification and the claims, all terms should be interpreted in the broadest manner possible consistent with the context, In particular, the terms "comprises" and "comprising" should be interpreted as referring to elements, components, or steps in a non-exclusive manner, indicating that the referenced elements, components, or steps may be present or utilized, or combined with other elements, components or steps that are not expressly referenced.

What is claim is:

1. An oral hygiene apparatus adapted to be installed on a sink comprising:
    a faucet water supply having two hose, a mixing valve coupled to the two hoses and a T-connector having an inlet, a first outlet and a second outlet;
    a faucet spout coupled to said first outlet and including a valve; and
    an oral hygiene-ware coupled to said second outlet having a flexible hose, a handle, and a plurality of exchangeable tips;
    wherein the handle includes a passageway, a valve and a quick connector arranged for quickly exchanging any one of the plurality of exchangeable tips;
    wherein the plurality of exchangeable tips each having an inlet side adapted for fastening to said handle and a hygiene end;
    wherein one of the plurality of exchangeable tips having a pipe with a male external thread and a cap with a female internal thread and a pinhole centrally located at a top of the cap disposed at the hygiene end being arranged such that said pipe includes a mechanism that divides single water flow into two separate flows that twist with respect to each other; and
    wherein when the cap is screwed tightly against the pipe, water ejects out from said pinhole in a shape that both opens a user's periodontal pocket to wash out any plaque therein and sucks out any plaque therein and when the cap is screwed loose with respect to the pipe, water ejects out from the said pinhole in the form of a water beam that cleanses a user's interdental area.

* * * * *